US008425491B2

(12) United States Patent
Tanghoj et al.

(10) Patent No.: US 8,425,491 B2
(45) Date of Patent: Apr. 23, 2013

(54) RETENTION ELEMENT FOR TELESCOPIC DEVICE

(75) Inventors: Allan Tanghoj, Kokkedal (DK); Soeren Boegvad Petersen, Glostrup (DK)

(73) Assignee: Coloplast A/S, Humlebaek (DK)

( * ) Notice: Subject to any disclaimer, the term of this patent is extended or adjusted under 35 U.S.C. 154(b) by 974 days.

(21) Appl. No.: 11/920,144

(22) PCT Filed: May 15, 2006

(86) PCT No.: PCT/DK2006/050021
§ 371 (c)(1),
(2), (4) Date: Jun. 23, 2009

(87) PCT Pub. No.: WO2006/119781
PCT Pub. Date: Nov. 16, 2006

(65) Prior Publication Data
US 2009/0318900 A1  Dec. 24, 2009

Related U.S. Application Data (60) Provisional application No. 60/713,723, filed on Sep. 6, 2005.

(30) Foreign Application Priority Data

May 13, 2005 (DK) ................................. 2005 00707
Sep. 6, 2005 (DK) ................................. 2005 01245

(51) Int. Cl.
*A61M 27/00* (2006.01)
(52) U.S. Cl.
USPC ........... 604/544; 604/250; 604/247; 604/104; 604/174; 604/256; 604/239; 604/329; 604/540; 600/29; 600/30; 600/31

(58) Field of Classification Search ............... 604/54, 604/55, 540, 544
See application file for complete search history.

(56) References Cited

U.S. PATENT DOCUMENTS

| 4,026,298 | A | 5/1977 | Grausz |
| 4,351,351 | A | 9/1982 | Flory et al. |
| 5,141,014 | A | 8/1992 | Poli et al. |
| 7,039,450 | B2 * | 5/2006 | Duarte ................ 600/374 |
| 2003/0060807 | A1 * | 3/2003 | Tanghoj et al. ........... 604/544 |

FOREIGN PATENT DOCUMENTS

| DE | 3816906 | * 11/1989 |
| DE | 3816906 A1 | 11/1989 |
| DE | 19610018 | 10/1996 |

(Continued)

*Primary Examiner* — Tatyana Zalukaeva
*Assistant Examiner* — Ilya Treyger
(74) *Attorney, Agent, or Firm* — Coloplast Corp., Coloplast A/S; Daniel G. Chapik; Nicholas R. Baumann (57) ABSTRACT

The present invention relates to a telescopic device comprising at least two sections, wherein an extraction force is needed to extend the device from a short telescope configuration to an extended configuration and securing the sections in extended configuration; a separation force is needed to pull the at least two sections apart; retention means coupling at least one of the two sections to at least one attachment point; and the uncoupling strength of the retention means is larger than the extraction force but smaller than the separation force. This allows the telescopic device to be properly extended into its extended configuration before the retention means uncouples the telescopic device from the at least one attachment point.

10 Claims, 9 Drawing Sheets

FOREIGN PATENT DOCUMENTS

| | | |
|---|---|---|
| EP | 1 518 574 A2 | 3/2005 |
| JP | 62-186869 | 8/1987 |
| JP | 03-073168 | 3/1991 |
| WO | WO 03/002179 A2 | 1/2003 |

* cited by examiner

RETENTION ELEMENT FOR TELESCOPIC DEVICE

This is a national stage of PCT/DK06/050021 filed May 15, 2006 and published in English, claiming benefit of U.S. provisional application No. 60/713,723 filed Sep. 6, 2005.

FIELD OF THE INVENTION

The present invention relates to a telescopic device provided with a retention element for extraction of the telescopic device.

BACKGROUND

Catheters for draining the bladder are increasingly used for intermittent as well as indwelling or permanent catheterization. Typically, catheters are used by patients suffering from urinary retention or by disabled individuals like para- or tetraplegics who may have no control permitting voluntary urination and for whom catheterization may be the way of urinating.

Catheterization is thus increasingly becoming a daily-life procedure significantly improving quality of life for a large group of patients.

Existing catheters are made from a single piece of a continuous catheter tube. The outer diameter of the catheter tube is typically constant throughout its length.

The length of the catheter enables insertion of a certain length into the urethra until urine starts to flow. At this point a certain over-length of the catheter should be available. The over-length enables the user to firmly hold the catheter, to guide urine to a place of disposal and to withdraw the catheter safely and without any risk of the catheter disappearing into the urethra.

It is important that the catheter does not collapse or kink and thereby blocks the passage for urine to drain through the catheter. Existing catheters are therefore typically made from a form stabile and relatively hard but still bendable tube, e.g. made from PVC, PU, PE, silicone or latex. Since the hardness of the tubes is selected relatively high with the view to avoid kinking, the catheters may collapse if they are bent in too small radius or curvature.

Accordingly, existing catheters not only have a considerable length, but they are also typically packed in an elongate condition. Therefore, the existing catheters may be troublesome to handle and to bring along, not least for individuals for whom catheterization is a daily-life procedure, wherein catheterization takes place several times a day.

WO 03/002179 A2 discloses a catheter comprising two catheter sections arranged in a telescopic fashion, a first one of the catheter sections may be intended for insertion into the human urethra, whereas a second one of the catheter sections is usually intended for forming a prolongation of the catheter outside the human urethra during use of the catheter. In use, that is in a first mutual configuration of the two catheter sections, the second catheter section preferably coextends with the first catheter section away from a distal end of the first catheter section. In a second mutual configuration, which usually is the configuration in which the telescopic kit is stored and transported, at least a portion of the first catheter section may be surrounded by the second catheter section. In order to allow the user to pull the first catheter section out of the second catheter section without touching the insertable part of the catheter, a container may preferably be provided to engage the first catheter section in a locking engagement. Thereby, it will be allowed to use the container to pull the first catheter section out of the second catheter section. The second catheter section is sealed by a first sealing closure and a second sealing closure, the second sealing closure being provided with internal and radially inwardly extending projections adapted for engaging a catheter eye. Thus, the second sealing closure engages the first catheter section by means of the inwardly extending projection for easy withdrawal of the first catheter section.

Existing catheters are designed to minimize the risk of sores in the mucous membrane and to give substantially no sensation of pain during insertion. Accordingly, known catheters are typically provided with a smooth and slippery surface optimized for safe and comfortable insertion into the urethra. Therefore, it may often be difficult, not least for a disabled user, to handle the catheter by manipulation of the slippery over-length.

Thus, there is a need for a better way of fixating a first section of a telescopic device.

SUMMARY

It may be seen as an object of the present invention to provide a telescopic device, which can be easily extracted without touching or damaging the device.

Additionally, it may be seen as an object of the present invention to provide a telescopic device where it is easy and safe to realize that the telescopic device is maximally extended and secured.

As shown in the examples one way of solving the problems may be done by attaching e.g. a string (retention element) to the catheter (the telescopic device) and to a container, containing the catheter. By pulling the free end of the catheter, the catheter will extend until fully extended and the locking between the two sections has been completed. Then, as the pulling continues, the force increases and the breaking strength of the string will be overcome, and thus the string will break. As a consequence, the catheter is released from the container, and the string is pulled out from the catheter. The string leaves no (i.e. very insignificant) marks on the surface of the catheter and the coating is still left practically intact.

DETAILED DISCLOSURE

Thus, one aspect of the invention relates to a telescopic device comprising at least two sections, wherein an extraction force is needed to extend the device from a short telescope configuration to an extended configuration and securing the sections in extended configuration; a separation force is needed to pull the at least two sections apart; retention means coupling at least one of the two sections to at least one attachment point; and the uncoupling strength of the retention means is larger than the extraction force but smaller than the separation force.

This allows the telescopic device to be properly extended into its extended configuration before the retention means uncouples the telescopic device from the at least one attachment point.

The uncoupling strength is the strength which should be overcome in order to uncouple the at least one section from the at least one attachment point, thereby allowing relative movement between the section of the telescopic device which was attached to the attachment point and the attachment point.

In one embodiment of the telescopic device according to the invention the retention means comprises at least one retention element attached to at least one of the two sections and to at least one attachment point provided on a retaining member; and the breaking strength of the retention element is larger than the extraction force but smaller than the separation force.

This has the effect that the detachment of the telescopic device from the attachment point is determined by the breaking strength of the retention element, which advantageously is relatively easy to determine, and only changes minimally during periods of storage etc. Furthermore, by breaking the retention element instead of for example uncoupling the element it is prevented that the retention element and the retaining member is reused.

It should be understood that the retention element may be a one-piece element, which for example may be formed by injection molding or extruding a plastic although other ways to produce suitable one-piece elements may be anticipated by the person skilled in the art. Furthermore, it should also be understood that the breaking strength of the retention element is the strength at which the retention element will break into at least two pieces. As mentioned this strength is easy to determine and is easy to reproduce within a small tolerance making it suitable for mass production.

It should be understood that the retention element may also be formed of a number components, for example through two component injection-molding or mechanically assembling two components. However, when used as retention element it will break at a point in such a way that it will not be possible to simply reattach the telescopic section and the attachment point without having to perform considerable repairing which is not intended.

The retention element attaches at least one of the two sections to at least one attachment point provided on a retaining member. This prevents relative movement between the section to which the retention element is attached and the retaining member. Relative movement is thereby first possible after breaking the retention element. Thus, a telescopic device according to the present embodiment is more stable against deformations compared to retention means where the coupling between the telescopic catheter and the retaining member is provided by two separate parts engaging with each other. Such a retention means may in case of deformation shift relative to each other and thus undesirably influence the uncoupling strength.

The present invention is described by way of example using a catheter and a straw as examples. However, the scope of the invention is by no means limited by these examples. The skilled person will appreciate the invention in other applications.

A telescope, as used herein, comprises at least two sections with different cross-sectional area placed inside each other. The telescope can be in a compacted configuration, where the sections are retracted maximally inside each other, or in an extended configuration, where the sections are maximally extracted to maximum length of the telescope, and an undefined number of intermediate positions between the compacted and the extended configuration. In the short and compacted telescope configuration, the at least two sections lie substantially one inside the other, for example the section for attachment inside another section or vice versa. The term 'short' with regard to the configuration is typically also called 'collapsed', 'compressed', 'retracted' or the like. The section for attachment is defined as the one section that is fixated at an attachment point by means of the retention element. The attachment point is defined as any possible attachment point providing a point of fixation so that the retention element can be secured at this attachment point, whereby the telescopic device being connected with the retention element is fixated in one end. Thus, the attachment point and the retention element provide a way of holding on to an end of the telescopic device while pulling the telescopic device towards the extended configuration.

In a preferred embodiment of the invention the prolongation section is defined as the opposite section in relation to the section for attachment. In the example of the catheter this means that the prolongation section is the distal end of the catheter in relation to the proximal end of the catheter that is to be inserted into the urethra. Since this distal end is typically provided with an over-length, which is not inserted into the urethra, the same needs for careful handling does not apply for the prolongation section as they do for the section for attachment.

Thus, in one further embodiment the telescopic device is a catheter having a proximal section and a distal section, the retention element being attached to the proximal section and wherein the retaining member is a container for containing the catheter.

In one embodiment of the invention, the telescopic device is hollow. Thus, the telescopic device can be used as a transport medium of for example gas or liquid.

In one embodiment the invention relates to a telescopic device, wherein the sections are hollow providing throughflow. Thus, a passageway for fluid or gas is provided through the telescopic device.

In one aspect the invention relates to a telescopic device, wherein the telescopic device has an inlet in a proximal section and an outlet in a distal section.

In a preferred embodiment the invention relates to a telescopic device, wherein the device is a medical device. This could for example be an endoscope or a gastroscope.

In one preferred embodiment, the telescopic device is a catheter. The examples as particulars of this description will be exemplified with a telescopic catheter. However, the skilled person will realize that the same principles will apply to other devices as well.

One preferred embodiment of the invention relates to a telescopic device, wherein the telescopic device is a urinary catheter.

As used herein a catheter has a proximal end for insertion into an opening and comprises an opening for draining a fluid into a conduit, the conduit extending towards an opposite distal end, the catheter comprising a proximal section and a distal section. Thus, the proximal end of the catheter is the end, which is intended for insertion into the urethra or another human orifice.

In one embodiment the telescopic device is a ready-to-use telescopic catheter. This is typically achieved by storing the catheter in a container together with a wetting fluid, which keeps the coating on the catheter wet, and thereby the catheter is smooth and easy to insert in e.g. the urinary channel immediately after opening the container.

Figure 7:
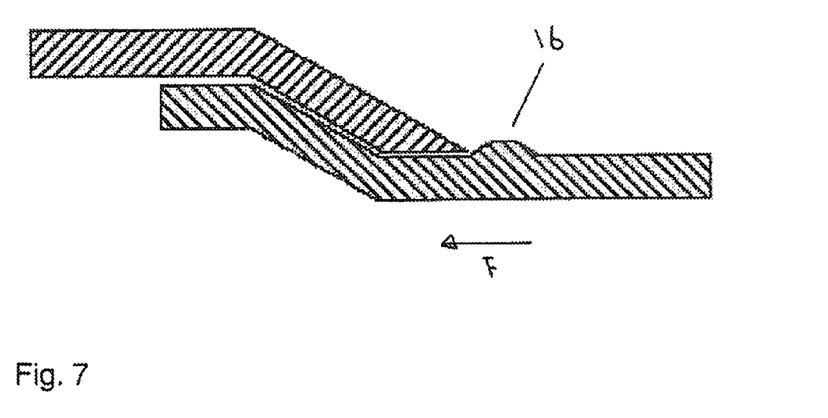
FIG. 7 shows a schematic partial cross section of a telescopic device provided with a bulb 16 to avoid that the telescopic device in the extended configuration collapses, when force is applied in the direction F on the section on which the bulb 16 is present. In the example where the telescopic device is a catheter, this force will be the push-in force that is applied when the catheter is inserted into the urethra.

The term extraction force is in this application used to describe the force needed to fully extend the telescopic device including the force needed to interlock two adjacent sections so that the telescopic device is maximally extracted and have reached the extended configuration. To interlock two adjacent sections the telescopic device is provided with securing means. In a preferred embodiment the telescopic device is provided with mechanical securing means. In a preferred embodiment the mechanical securing means is a bulb or a circular protrusion, as shown in FIG. 7, on a proximal section of the catheter. Such bulb will act as a mechanical lock between the distal and the proximal section of the catheter allowing movement in one direction but not in the other. It is important to provide a smooth transition point between the sections of the catheter in order not to injure the mucosa.

During insertion the bulb will 'lift' the mucosa to avoid contact with the point of transition. In a preferred embodiment the catheter is also provided with a second securing means for securing the catheter in the opposite direction in relation to the bulb so that the catheter in the extended configuration is secured in both directions.

The term separation force is in this application used to describe the force that is necessary to pull the at least two sections of the telescopic device apart, i.e. to fully separate the at least two sections to the point where they are no longer in contact with each other. For clarity it is noted that the extraction force and the separation force goes in the same direction.

In a preferred embodiment the breaking strength of the retention element is larger than the extraction force and smaller than the separation force. In another preferred embodiment the breaking strength is also smaller than the force needed to damage the telescopic device so that the retention element will break before any risk of the retention element cutting through or otherwise damaging the telescopic device occurs.

By pulling the free end of the telescopic device, the device will extend until fully extended and the locking between the at least two sections has been completed. Then, as the pulling continues, the force increases and the breaking strength of the retention element will be overcome, and thus the retention element will break. As a consequence, the telescope device is released from the retaining member, e.g. the container, and the broken retention element is pulled out from the catheter.

In a preferred embodiment the retention element, when exposed to a force equal or greater than the breaking strength of the retention element, will break into at least two separate parts.

An inserted surface coated catheter is pulled out of location, for example the human urethra, with a force of about 0.2N. For an uncoated catheter, this pull-out force is in the range of 2N. It is much preferred that the transition between the two sections of the catheter is constructed such that the transition will endure the pull-out force. Otherwise, the catheter could separate into two pieces and the proximal section remain in the urethra. The force needed to separate the catheter into at least two pieces is defined as the separation force.

Typically, the force required to insert a catheter, the push-in force, is about 1 N for a coated catheter. Thus, it is much preferred that the transition between two adjacent sections of the catheter is constructed such that the transition will endure the push-in force. Otherwise, the catheter could collapse into the non-extended configuration during insertion. As a rule of thumb, the ability to endure the push-in force must be so that the catheter will tend to bend when exposed to high push-in forces, before it will tend to collapse into the non-extended configuration. Forces of more than 10N are not required to insert a catheter.

A catheter will often have a hydrophilic coating on the outside to ease insertion and withdrawal from the urethra. By using the proposed retention element a way to hold on to one slippery section is provided. However, not only is it possible to hold on to the slippery catheter, but the holding itself will neither damage the coating nor the catheter. Too large areas with damaged (typically removed) coating will make it harder to insert and remove the catheter. A catheter with damaged areas in the coating might injure the inside of the urethra (the mucosa) and cause discomfort and bleeding.

A catheter is preferably sterile, when it is to be inserted into the human urethra, which is prone to infections. Therefore, it is important not to touch the sterile catheter upon extraction to the extended configuration prior to use. The present invention provides a means of extraction which enables the user to fully extract the catheter without touching the parts of the catheter, which are to come in contact with the urethra.

In the present invention the retention element, which is used to hold on to one section of the catheter upon extraction, does not cause any damage to the catheter during extraction. This means that the catheter surface is intact, thus minimizing the risk of injuring the urethra and the mucosa.

In another embodiment of the invention the telescopic device is a straw. The telescopic straw can be used in for example juice cartons for taking on trips etc. It is more hygienic to be able to extract the telescopic straw without touching it, and the present invention provides this advantage. Furthermore, the invention provides the advantage of knowing for sure when the straw is fully extended and secured, since the retention element will not break until the straw has reached the extended configuration and is secured. This eliminates problems with spilling the drink if the straw is not fully secured and therefore not sufficiently sealed at the transition point. Furthermore, since the breaking strength of the retention element is smaller than the separation force, the retention element will break and thereby indicate to the user that the fully extended configuration has been reached, thus eliminating the risk of pulling too hard when extracting the straw.

One embodiment of the invention relates to a telescopic device, wherein the section for attachment is the distal part of a catheter.

Another embodiment of the invention relates to a telescopic device, wherein the section for attachment is the proximal part of a catheter.

Figure 4A:
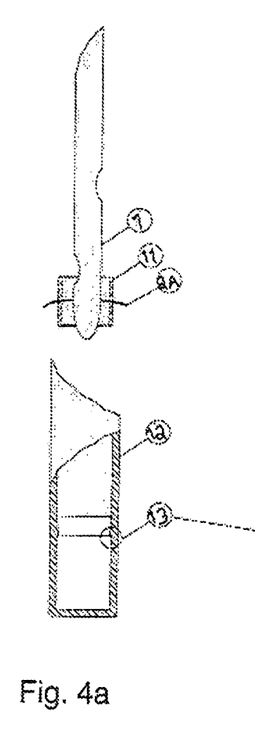
FIG. 4*a* shows a catheter 1 with a string 2A that is sewn both through catheter and the internal fixation ring 11. Below the catheter 1 is shown the product container 12, which is closed in the bottom end and has an internal recess 13.
Figure 4B:
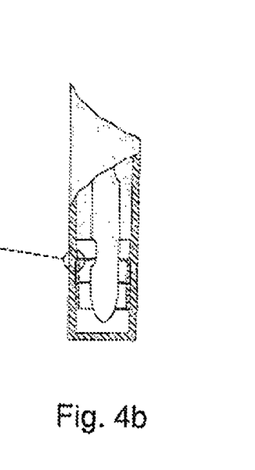
FIG. 4*b* shows the catheter with the string 2A and the internal fixation ring 11, which have been pushed into the product container 12, whereby the fixation ring 11 has been fixed below the recess 13 of the product container 12, and the string 2A has been fixed in the contact face between the internal fixation ring and the product container 12.

One aspect of the invention relates to a telescopic device, wherein the attachment point is located in a container. The container can preferably be injection moulded in e.g. PP. The container preferably protects the telescopic device after production and before use. In a preferred embodiment the container also protects the telescopic device during extraction so that the container covers at least part of the telescopic device during extraction. The attachment of the retention element to the container can be by use of an internal fixation ring so that the retention element is fixated between the inner surface of the container and the internal fixation ring, e.g. as illustrated in FIGS. 4a and 4b. One advantage of this embodiment is that the telescopic device can be placed in a completely sealed container, which is favorable if for example the telescopic device is stored in the container with liquid. This is also an advantage when for example the telescopic device is sterile, since the completely sealed container provides a contamination barrier. The internal fixation ring can for example be extruded/or injection moulded in PP.

Figure 3A:
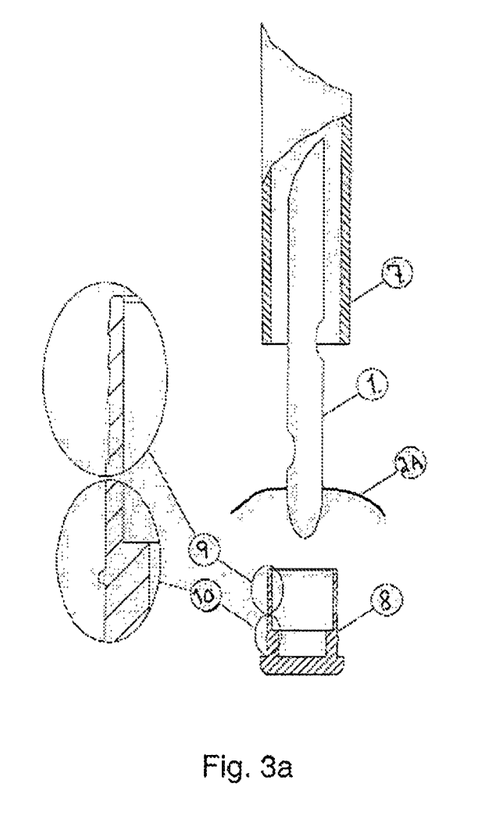
FIG. 3a shows a catheter 1 with a string 2A according to FIG. 1a placed inside a product container 7. Below the catheter 1 is shown an internal plug 8.
Figure 3B:
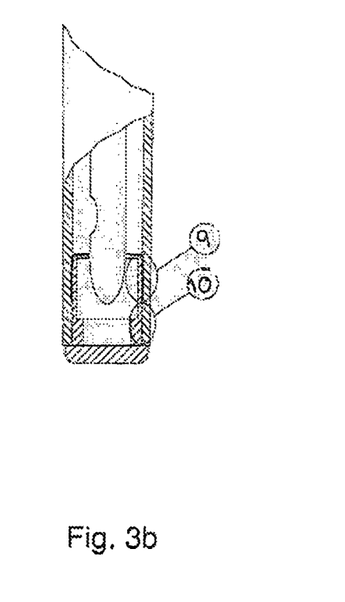
FIG. 3b shows the internal plug 8 assembled with the product container 7, the string 2A being fixated at a first contact face 9 between the internal plug 8 and the product container 7. At the same time a second contact face 10 between the internal plug 8 and the product container forms a seal.

Another aspect of the invention relates to a telescopic device, wherein the attachment point is located on a container. In a preferred embodiment the container is an open-end container with a corresponding internal plug as shown in FIGS. 3a-3b. The outer surface of the plug is in a preferred embodiment provided with for example ribs for improved gripping and sealing against the inner surface of the container. The retention element is in a preferred embodiment fixated between the inner surface of the container and the outer surface of the internal plug as illustrated in FIGS. 3a and 3b.

Figure 5A:
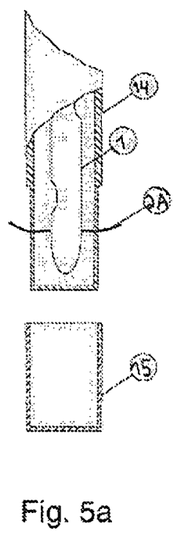
FIG. 5*a* shows a catheter 1 with a string 2A that is sewn both through the catheter and a product container 14 that is closed in the bottom end. Below the catheter 1 and the product container 14 is shown an external seal and fixation cap 15.
Figure 5B:
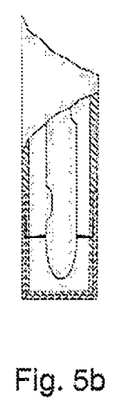

Another possibility is to let the retention element pass all the way through the catheter and the container and then fixate the retention element by means of a fixation cap or ring so that the retention element is fixated between the outer surface of the container and the inner surface of the fixation cap or ring as illustrated in FIGS. 5a and 5b for example. The fixation cap can for example be injection moulded in e.g. PP, and the fixation ring can for example be extruded or injection moulded in e.g. PP. The container can for example be injection moulded in e.g. PP with reduced wall thickness in the bottom end to ease penetration of the needle. In a preferred embodiment glue is applied on the retention element at the holes in the container, whereby the holes are sealed and the retention element fixated. As a further alternative a small amount of polypropylene (PP) may be welded onto the container in order to seal the holes, where the retention element passes through the container, and in order to fixate the retention element to the container.

One embodiment of the invention relates to a telescopic device, wherein the attachment point is located on a container for a soft drink. If for example the telescopic device is a straw on a container for at soft drink, one end of one section of the telescopic device may be fixated on the container so as to hold the one end of the one section of the telescopic device back until the telescopic device is fully extended. Thus, it is more hygienic to be able to extract the telescopic straw without touching it, and the present invention provides this advantage.

Figure 6A:
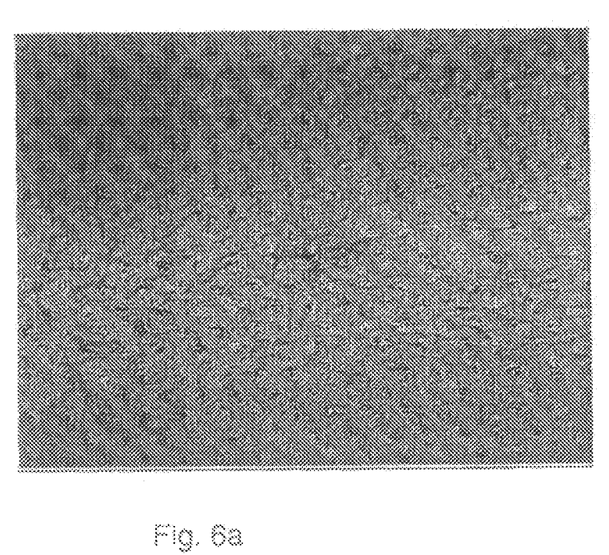
FIG. 6*a* shows a photograph of a catheter taken perpendicularly to the catheter surface on the place where the string 2A has penetrated the catheter.
Figure 6B:
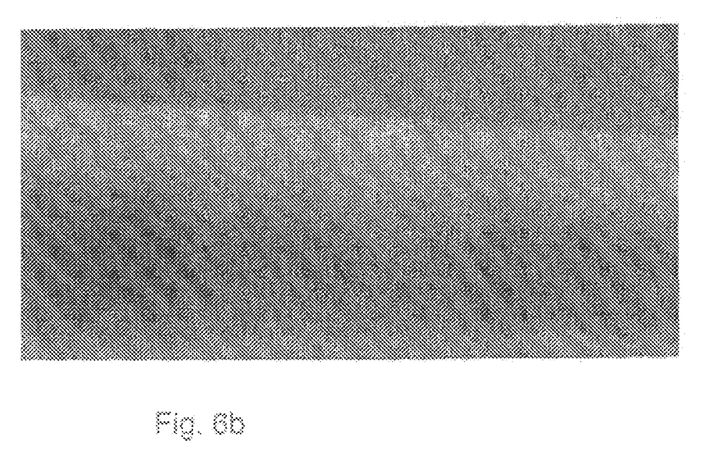
FIG. 6*b* shows a photograph of a catheter taken tangentially to the catheter surface on the place where the string 2A has penetrated the catheter.

One aspect of the invention relates to a telescopic device, wherein the retention element is a string. This is a preferred embodiment since the calculation of the force needed to free the telescopic device from the retention element is very simple, as it only relies on the breaking strength of the string. The breaking strength of a string is a well-defined characteristic and is known to the skilled person. Furthermore, a great variety of strings with different characteristics and breaking strengths is readily and commercially available. This presents a further advantage, since this feature does not require any additional tooling or special or extra manufacturing steps. The specific type of string can be chosen from a variety of strings suitable for the invention as for example known and available monofilament wires such as: suture (polypropylene) string, different types of (nylon) fishing line, polyester and poly-urethane wires. When the telescopic device is fully extended, and the applied pulling force exceeds the breaking strength of the string, the string will break, and the free, broken ends of the string slide out of the telescopic device. In the example of a coated catheter, the string leaves insignificant marks on the surface of the catheter and the coating is still left intact as shown in FIGS. 6a-6b.

In one embodiment of the invention the string forms an angle of less than 45° to the direction of extension of the telescopic device when the telescopic device is moved towards its extended configuration. It should be understood that the direction of extension is the direction in which the device extend from its short telescope configuration to its extended configuration; typically this direction will be parallel to the centre axis of the telescopic device. In an even more preferred embodiment, the string is generally parallel to the direction of extension.

This allows the breaking strength of the string to be even easier to determine as the angular force component of the string will be reduced as the angle between the extended string and the extraction direction is reduced. Furthermore, this will also provide a retention element which is suitable for mass production since the breaking strength of the string mainly will be determined by the characteristics of the string itself and not by outside factors such as the angle to which the string is attached to the telescopic section or the attachment point. This consequently makes a telescopic device according to the invention easier to reproduce.

In order to reduce the angle between the extended string and the extraction direction the string may in one embodiment be loose, i.e. the string is not tightly stretched between attachment points thus providing some slack, when no forces are applied to the string. This may for example be realized by using a string where the length of the string between the attachment points is at least two times the shortest length between attachment points, preferably at least four times. Providing sufficient length, and thereby slack making the string loose, the string can be stretched into almost parallel alignment to the extraction direction when the telescopic device is pulled towards its extended configuration, which as a consequence applies tension to the string.

In yet another embodiment the two ends of the string may be attached adjacent to each other at the same attachment point, attaching the telescopic section in a loop. This will also provide a small angle between the extended string and the extraction direction.

In one combined embodiment the ends of a loose string is attached at the same attachment point.

In another embodiment the invention relates to a telescopic device, wherein the retention element is a retention arrow as illustrated by example 4 and shown in FIGS. 8a-8e. The retention arrow can comprise a section 17, just below the conical part 18 of the arrow that has been weakened in terms of the traction force needed to rupture. Thus, when the pulling force applied on the telescopic device exceeds the breaking strength of the retention arrow at section 17, the retention arrow will break in the weakened area below the conical part 18 of the arrow. The broken retention arrow comprises the conical part 18 of the retention arrow 2B and a lower part 22 of the retention arrow 2B. In a preferred embodiment the telescopic device comprises a compartment 19 in a tip portion of the telescopic device so that the part of the broken arrow, which remains in the telescopic device after the device has been fully extended, does not come into contact with the main conduit 20 of the device (see FIG. 8d). By varying the breaking strength of section 17, the retention force can be adjusted as desired. In one embodiment free movement of the conical part 18 is impeded, after breakage of the retention arrow (to pass inside through the telescopic device), by tip forming the telescopic device so that the inner device diameter is reduced to below the outer diameter of the conical part 18 of the retention arrow 2B, e.g. 1.0 mm, relatively close to the Up of the telescopic device (see FIG. 8e) to provide an inner annular rib 21. Other embodiments of such means for impeding free movement of the conical part 18 could be one or more protrusions or projections on the inner surface of the telescopic device.

Alternatively the entire retention arrow can be drawn out of the telescopic device in one piece. Thus, the telescopic device and/or the retention arrow yields by the applied pulling force when the pulling force exceeds the retention force. In this case a suitable maximum arrow diameter D(a) is chosen to adjust the retention force.

In a preferred embodiment of the invention the string goes all the way through the telescopic device, and both its ends are fixated at the at least one attachment point. Thus, it is the middle of the string that runs through the telescopic device. This provides an advantage in that when the string breaks, no material, as for example a piece of the string, is left in the telescopic device. The broken string simply slides out of the telescopic device after it breaks.

In one aspect the invention relates to a telescopic device, wherein the retention element is a glue.

One embodiment of the invention relates to a telescopic device, wherein the retention element is attached to a section for attachment through the eyes of the catheter. This particular embodiment provides an additional advantage in that it makes use of the existing eyes of the catheter so that no further penetration of the catheter wall is needed. Thus, any risk of damaging the catheter by additional penetration is minimized. One alternative to guiding the retention element through the catheter eyes is to guide the retention element through pre-made holes (with a diameter of e.g. 0.5-0.8 mm) placed approximately midway between the tip of the catheter and the closest catheter eye.

A so-called eye of a catheter is an opening/hole formed on the side of the catheter, typically on the part of the catheter which is inserted into e.g. the urinary channel and typically the eye(s) is(are) placed close to the proximal end of the catheter, i.e. the end which is inserted farthest into the body.

Another aspect of the invention relates to a telescopic device, wherein the retention element is attached to the section for attachment by sewing through the catheter. By use of sewing with a needle the area of penetration is minimized so that the catheter and the possible coating of the catheter are not damaged as illustrated in example 1 and FIGS. 6a-6b. Sewing the retention element in the catheter is further advantageous because the catheter does not have to be orientated in a specific way. An additional manufacturing step for orientation of the catheter would be time-consuming, thus this provides a significant advantage since speed of manufacturing is cost-essential in catheter manufacturing.

In a preferred embodiment the invention relates to a telescopic device, wherein the telescopic device is a catheter for men. Catheters for men are typically longer than catheters for women, because of the difference in length of the male and female urethra. The length of the male urethra in combination with the need for a compact catheter makes the present invention very advantageous in relation to catheters for men. The length of the male urethra is typically longer than the desired short configuration of a telescopic catheter, i.e. more than one section of the telescopic catheter has to be inserted into the urethra. This means that the transition between one section to another has to be as smooth as possible not to irritate the urethra during insertion. Thus, the present invention provides a compact catheter that is very suitable as a catheter for men.

As discussed previously it should be understood that the relationship between the extraction force, the breaking strength and the separation force is important in order to properly and safely handle the telescopic device.

The extraction force is the force required to move the telescopic sections relative to each other in order to place the section in an extended configuration ready to use; the breaking strength is the strength that has to be exceeded in order for the retention element to break; and the separation force is the force required to move the telescopic sections relative to each other in order to the section apart generally leaving the telescopic device useless.

Thus in one embodiment the extraction force may advantageously be between 0.1 N and 5 N, the breaking force may be between 1 N and 15 N and the separation force is above 50 N. It should be understood that the ranges within specific embodiments should not overlap each in order to provide reliable functionality of the telescopic device.

In a preferred embodiment the invention relates to a telescopic device, wherein the breaking strength is in the range of 1-10 N.

In another preferred embodiment the invention relates to a telescopic device, wherein the breaking strength is in the range of 1-5 N.

In still another preferred embodiment the invention relates to a telescopic device, wherein the breaking strength is in the range of 1-3 N.

In one aspect the invention relates to a method for producing a telescopic device comprising the steps of
(a) providing a telescopic device;
(b) attaching retention element to the telescopic device of (a); the retention element having a breaking strength that is smaller than the separation force, the force needed to pull the two sections of the telescopic device apart, and a breaking strength that is larger than the extraction force, the force needed to extend the device from a short telescope configuration to an extended configuration including securing the sections in extended position;
(c) attaching the retention element to an attachment point.

In another aspect the invention relates to a method for producing a telescopic device comprising the steps of
(a) providing a telescopic device;
(b) measuring the extraction force, the force needed to extend the device from a short telescope configuration to an extended configuration including securing the sections in extended position;
(c) measuring the separation force, the force needed to pull the two sections of the telescopic device apart;
(d) providing retention element with a breaking strength that is smaller than the separation force and larger than the extraction force;
(e) attaching the first part of the retention element to the telescopic device;
(f) attaching the second part of the retention element to an attachment point.

As an example of how to provide a telescopic catheter the following method can be followed.

Manufacturing the section for attachment (proximal end/section):
1) Take an extruded PUR tube—and cut in the length for the section for attachment.
2) Tip form—e.g. by induction heating a nickel form—the proximal end to form a rounded (e.g closed) end.
3) Form—e.g. by induction heating in a nickel form—a mechanical securing means—on the distal end—being a gradual increase in the diameter of the section for attachment to form a conical outside shape.
4) Punch holes in the catheter wall close to the tip end (the proximal end) to form catheter eyes.
5) Optionally coat the section for attachment with a hydrophilic coating.

Manufacturing the prolongation section (distal end/section):
1) Take an extruded PUR tube and cut in the length for the prolongation section.
2) Form—e.g. by induction heating in a nickel form—a mechanical securing means on the distal end.
3) Form—e.g. by induction heating in a nickel form—a mechanical securing means—on the proximal end—being a gradual decrease in the diameter of "the second section" to form a conical inside shape.
4) Optionally coat the prolongation section with a hydrophilic coating.

Insert the section for attachment, with the proximal end first, into the distal end of the prolongation section.

Both the section for attachment and the prolongation section may alternatively be manufactured by moulding techniques.

A catheter can for example be manufactured from the following materials: silicone or a thermoplastic elastomeric material, other thermoplastic materials, curable elastomeric materials, polyamide resins or elastomers or any mixture thereof, i.e. the group may comprise materials like, PA (polyamide), PP (polypropylene), PVC (polyvinylchloride), PU (polyurethane), PE (polyethylene), latex, Pebax™ and/or styrenic block co-polymers like Kraton™, The measuring of the extraction force as well as the separation force can for example be done by use of spring scale or tensile strength equipment.

The retention element can for example be a string, a glue, a retention arrow or any other suitable retention element which will be appreciated by the skilled person.

In one preferred embodiment the invention relates to a method, wherein the telescopic device is a catheter.

In another preferred embodiment the invention relates a method, wherein the telescopic device is a catheter for men.

In yet another aspect the invention relates to a use of retention means for attaching a section of a telescopic device to an attachment point wherein the retention element breaks after the telescopic device has been moved to an extended configuration. It should be understood that the retention means used may among others be the retention means and retention elements described herein.

EXAMPLES

Example 1

Analysis of Catheter after Attachment and Deployment of Retention String

Figure 1A:
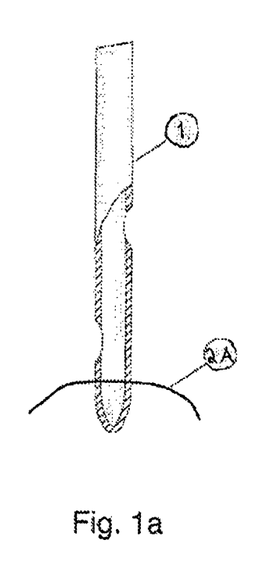
FIG. 1a shows one preferred embodiment of the invention, where the retention element 2 in the shape of a string goes all the way through the walls of the catheter 1, thereby attaching the string to the proximal section of the catheter.

Attachment of retention string to catheter:
1) Was done as shown in FIG. 1a using:
   a) a standard Ch12 (French Size) Coloplast (PUR) non hydrophilic coated catheter.
   b) a Suture Prolene 6/0 string.
Attachment of retention string to product container:
2) Was done as shown in FIGS. 3a-3b.
Pulling the catheter to rupture of attachment string:
3) A "Salter Super Samson" spring scale was attached to the connector end of the catheter: with the catheter inside the product container—being attached by the string 2A to the product container.
4) The spring scale was pulled slowly by one hand while holding the product container by the other hand, until the string ruptured and the catheter was released from the product container. The rupture force, i.e. the breaking strength, was read on the spring scale.
Examining the surface of the catheter by microscope:
5) Within 1 minute after finishing item 4 the catheter surface (where the string had penetrated the catheter) was examined using a Nikon SMZ800 stereo microscope (Nikon DN100 camera and Lucia net v.1.16.5 software) and a magnification of app. 25. The examination was done:
   a) Perpendicular to the catheter surface, see FIG. 6a, and
   b) Tangential to the catheter surface, see FIG. 6b.
The examination showed that the formed hole(s) are very small with basically no opening through the catheter wall.

Examining the surface of the catheter with finger and tongue:
Following item 5 the catheter surface was examined by slowly sliding:
   a) a finger and subsequently
   b) the tongue
over the place where the string had penetrated the catheter.
This verifies that this place may actually not be identified/distinguished from the rest of the catheter surface.

Example 2

Testing of the Breaking Strength of the String

Using a catheter with a string sewn through (FIG. 1a) and fixating the string 2A to the product container as shown in FIGS. 3a and 3b—the maximum pulling force—at which the string breaks, e.g. the breaking strength—has been measured with a "Salter Super Samson" spring scale (0-5 kg):

| Sample | Maxima Perfexion Fishing line | Suture Prolene 5/0 | Suture Prolene 6/0 |
| --- | --- | --- | --- |
| 1 | app. 2 kg | app. 1.7 kg | app. 0.8 kg |
| 2 | app. 2 kg | app. 1.8 kg | app. 0.9 kg |

Example 3

Testing Breaking Strength Changes Due to Sterilization and Storing

In one embodiment the telescopic device is a telescopic catheter, which between production and use is stored in a container. For medical use, such as for example a urinary catheter, the catheter needs to be sterilized before use and it has been tested to see what influence sterilization has on a retention element in the shape of a string.

The test was carried out on a Lloyds tensile testing machine with three different types of strings:

| Manufacturer | Material | Diameter [mm] | Type |
| --- | --- | --- | --- |
| Sidearc | PET(polyethylene terephthalate) | 0.10 | Monofilament |
| Sidearc | PET | 0.08 | Monofilament |
| Rhodia | PET | 0.12 | Monofilament |

The breaking strength of each of the three types of strings was measured twenty times for each string in the following three situations:
1. String as provided from manufacturer.
2. String E-beam sterilized at 2×40 kGy while in PVP (poly-vinyl-pyrrolidone) water.
3. String E-beam sterilized at 2×40 kGy while in PVP water and aged for 7×24 hours at 40° C.

The test showed the following results:

| Situation | Sidearc [0.08 mm] | | | Sidearc [0.10 mm] | | | Rhodia [0.12 mm] | | |
| --- | --- | --- | --- | --- | --- | --- | --- | --- | --- |
| | 1 | 2 | 3 | 1 | 2 | 3 | 1 | 2 | 3 |
| Mean of breaking strength over 20 measurements [N] | 2.96 | 2.87 | 3.05 | 4.73 | 4.15 | 4.61 | 6.07 | 5.53 | 6.26 |
| Standard deviation [N] | 0.13 | 0.15 | 0.17 | 0.11 | 0.19 | 0.15 | 0.46 | 0.28 | 0.20 |

It may be appreciated that especially in situations 1 and 3 the breaking strength deviates very little. It is furthermore situations 1 and 3, which are the most relevant situations to consider, as it typically will take at least a few days for the products to be available to users.

Thus it would indicate that when using strings of the type mentioned above the breaking strength varies very little from specimen to specimen and after the string has been sterilized the breaking strength varies very little which is advantageous for mass production. Especially it shows that the standard deviation between batches of strings is very low and thus using a string as a retention element will provide a breaking strength which may be highly reliable and almost the same from product to product.

Example 4

Retention Arrow

Figures 8A, 8B:
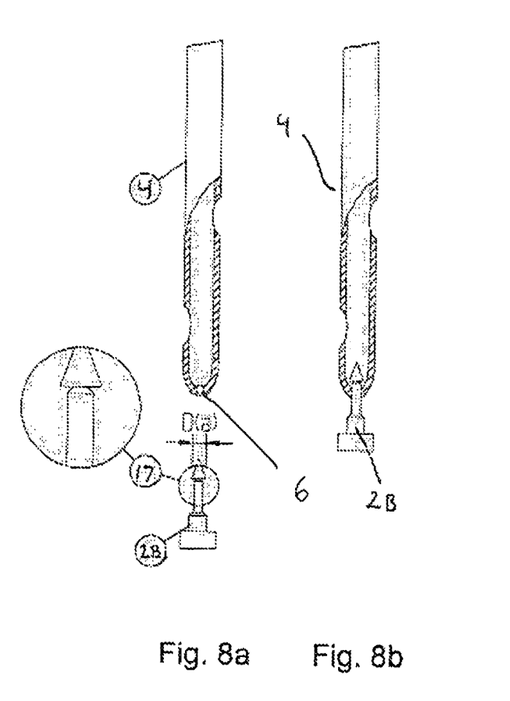
FIG. 8*a* shows a catheter 4 with a tip containing a separate hole 6 where the centerline of the hole 6 is parallel to the longitudinal axis of the catheter 4. Below the catheter 4 is shown the retention arrow 2B. The retention arrow comprises a section 17, just below the conical part, that is weakened in terms of traction force needed to rupture.
FIG. 8*b* shows the catheter 4 of FIG. 8*a*, where the retention arrow 2B has been pushed into the catheter 4 through the separate hole 6 in the catheter 4.
Figure 8C:
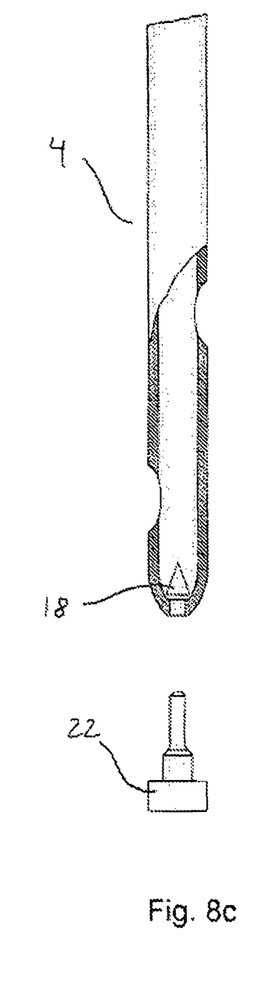
FIG. 8*c* shows the catheter 4 of FIGS. 8*a* and 8*b*, where the retention arrow 2B has been broken, and the conical part 18 of the retention arrow 2B lies inside the catheter 4. The lower part 22 of the retention arrow 2B is shown below the catheter 4.
Figure 8D:
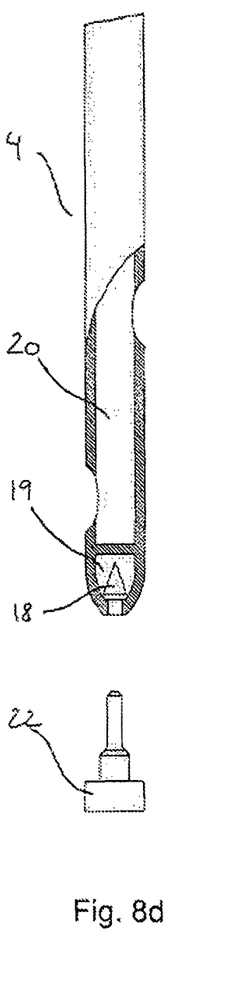
FIG. 8*d* shows the catheter 4 of FIGS. 8*a* and 8*b*, where the retention arrow 2B has been broken, and the conical part 18 of the retention arrow 2B lies inside the catheter 4 in a compartment 19 so that the part of the broken retention arrow 2B, which remains in the telescopic catheter, does not come into contact with the main conduit 20 of the catheter 4. The lower part 22 of the retention arrow 2B is shown below the catheter 4.
Figure 8E:
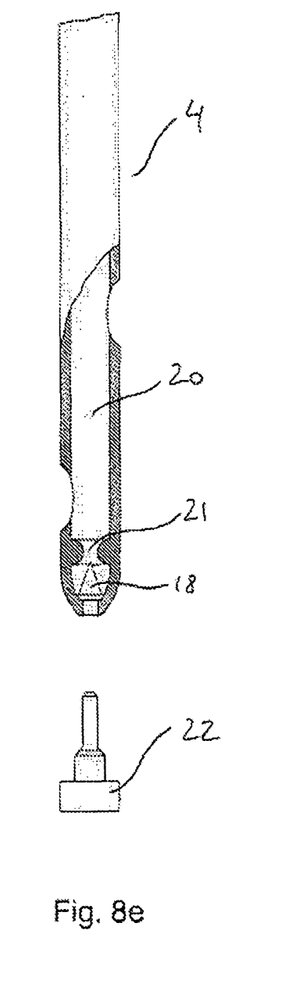
FIG. 8*e* shows the catheter 4 of FIGS. 8*a* and 8*b*, where the retention arrow 2B has been broken, and the conical part 18 of the retention arrow 2B lies inside the catheter 4. The inner surface of the catheter 4 is provided with an annular rib 21 preventing the conical part 18 of the retention arrow 2B from entering the main conduit 20 of the catheter 4. The lower part 22 of the retention arrow 2B is shown below the catheter 4.

1) A catheter 4 (made from PUR, size (French) ch12, see FIG. 2) is tip formed to have a separate hole 6 at the tip of the catheter (app. 0.8 mm diameter) using an induction heating tip forming tool (Nickel).
2) The catheter is optionally hydrophilic coated.
3) Subsequently the retention arrow 2B (e.g. injection moulded in PP with a diameter D(a) of e.g. 1.6 mm), is pushed with the pointy end through the separate hole 6.
4) When pulling the catheter 4, the retention arrow 2B breaks, and the conical part remains inside the catheter (tube), see FIGS. 8c, 8d and 8e.

DESCRIPTION OF THE FIGURES

This is typically done by using a sowing needle (not shown) in order to easily pierce the walls of the catheter and guide the string through. One such example of performing such a 'sowing' procedure is described in the following five steps:
1) A standard hydrophilic coated catheter 1 (made from PUR (polyurethane), size (French) ch12 with rounded tip and two catheter eyes 3 was used.
2) Using a "Major 6600" sewing machine and a Prym no. 70/10 (Jeans standard) needle, the string: Ethicor/Prolene 6/0 or 5/0 (monofilament polypropylene surgical suture) or Maxima Perfexion (0.11 mm fishing line) was sewn through the catheter approximately midway between the tip of the catheter and the closest catheter eye. Alternatively, polyester monofilament wire, diameters 0.12-0.15 mm, type: M183 from Rhodia, can be used.
3) Once the needle with the string had passed through the catheter—and before reversing the needle movement to pull the needle back out of the catheter—the string was fixed/held on the exit side (where the needle came out) of the catheter—to avoid that the string was pulled back through the catheter together with the needle.
4) The needle was then pulled out of the catheter and the string was cut so that approximately 20-40 mm of string was hanging out of the catheter on either side.
5) The catheter was then ready for the string to be attached to the attachment point(s).

Figure 1B:
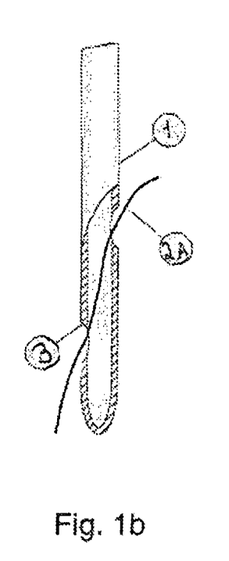
FIG. 1b shows another embodiment of the invention, where the retention element 2 is guided through the catheter eyes 3, thereby attaching the string to the proximal section of the catheter.

This may for example be achieved through the following five steps:
1) A standard hydrophilic coated catheter 1 (made from PUR, size (French) ch12 with rounded tip and two catheter eyes 3 is used.
2) Using a sewing machine and a needle without a sharp end, the string is guided through the catheter—by entering one catheter eye and passing out through the other catheter eye.
3) Once the needle with the string has passed through the catheter—and before reversing the needle movement to pull the needle back out of the catheter—the string is fixed/held on the exit side (where the needle came out) of the catheter—to avoid that the string is pulled back through the catheter together with the needle.
4) The needle is then pulled out of the catheter and the string cut so that approximately 20-40 mm of string is hanging out of the catheter on either side.
5) The catheter is now ready for the string to be attached.

FIG. 2b shows the embodiment of the invention in FIG. 2a. The retention arrow 2B has been pushed into the catheter through the end hole 6. This is how the catheter 4 and the retention arrow 2B would be positioned relative to each other after the last manufacturing step and before the catheter is telescopically extended for use. This provides retention means where coupling between the telescopic catheter and the retaining member is provided because the retention arrow and the catheter section engage with each other.

Figure 2A:
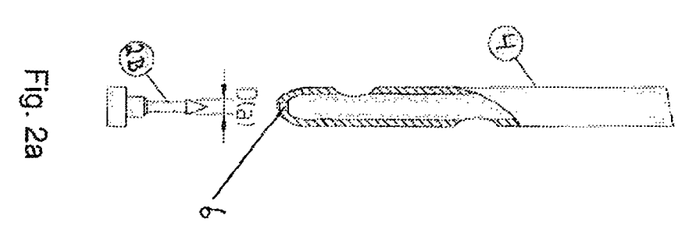
FIG. 2a shows another embodiment of the invention, where a catheter 4 with a tip comprising an end hole 6 where the centerline of the hole is parallel to the longitudinal axis of the catheter. Below the catheter is shown the retention arrow 2B.
Figure 2B:
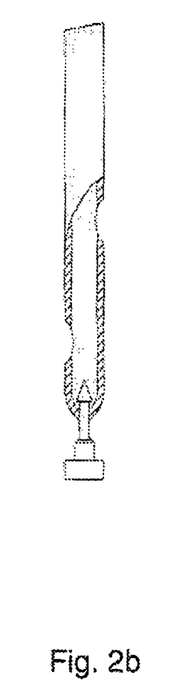

The telescopic device as shown in FIGS. 2a and 2b may thus be formed according to these following two steps:
1) A catheter 4 (made from PUR, size (French) ch12, see FIG. 2) was Up formed to have a separate hole at the tip of the catheter (app. 0.8 mm diameter) using an induction heating tip forming tool (Nickel).
2) Subsequently the retention arrow 2B (manufactured in POM (PolyOxyMethylen) by machining) is pushed with the pointy end through the separate hole 6.

By varying the maximum arrow diameter D(a): 1.35-1.75 mm, the uncoupling strength can be adjusted as desired.

Typically the embodiment of FIGS. 3a and 3b may be formed as follows:
1) A catheter with a string, for example as described in relation to FIGS. 1a and 1b.
2) A product container 7 (made by SLA: could be injection moulded in e.g. PP) with a hole in the bottom end was used.
3) An internal plug 8 (made by SLA: could be injection moulded in e.g. PP) was used.
4) The catheter with string was pushed with the tip end through the bottom hole of the product container.
5) The internal plug 8 was then pressed half way into the bottom hole of the product container.
6) At this point the string 2A was cut—so that no string was outside the product container.

7) Subsequently the internal plug 8 was pressed all the way into the product container (as illustrated in the FIG. 3.*b*).

In order to attach the retention string to a product container using and internal fixation ring the following steps may be performed in a specific embodiment:
1) A catheter 1, a string 2A, and an internal fixation ring is used.
2) A product container 7 that is closed in the bottom end is used.
3) The string 2A is sewn through both catheter and internal fixating ring as shown in FIG. 4*a*.
4) The fixating ring with catheter (and string) is then pushed into the product container—so far that the internal fixating ring passes the recess 13 in the product container—whereby it is fixated in the product container as shown in FIG. 4*b*.

FIG. 5*b* shows a catheter, where the external seal and fixation cap is pushed over the bottom end of the product container, whereby the string 2A is fixated in the interface/contact face between the production container and the external seal and fixation cap, while at the same time sealing the holes in the product container, where the string 2A passes through.

In one specific embodiment the retention string is attached to the product container by using an external seal and fixation cap or ring by the following steps:
1) A catheter 1, a string 2A, an external seal and fixating cap 15 and a product container 14 that is closed in the bottom end is used.
2) The string 2A is sewn through both catheter and the bottom end of the product container, as shown in FIG. 5*a*.
3) The external seal and fixation cap 15 is then pushed onto the bottom end of the product—being fixed either by e.g. friction or gluing.
Alternatively:
a) the external seal and fixation cap 15 is a ring
b) instead of using an external ring (or seal and fixation cap)—glue (e.g. Loctite 4304) is applied on the string 2A at the holes in the product container—whereby the holes are sealed and the string 2A fixated. Alternatively a small amount of PP is welded onto the product container—to close the holes where the string 2A passes through the product container—and to fixate the string 2A to the product container.

The invention claimed is:

1. A telescopic device comprising:
a urinary catheter disposed in a container, the urinary catheter provided with an inlet in a proximal section and an outlet in a distal section, wherein
an extraction force extends the urinary catheter from a short configuration to an extended configuration and secures the sections in the extended configuration,
a separation force separates the urinary catheter apart from the container,
retention means coupling at least one of the two sections to at least one attachment point provided with the container,
where an uncoupling strength of the retention means is larger than the extraction force but smaller than the separation force,
a retention element attached between the proximal section and the attachment point, and
a breaking strength of the retention element is larger than the extraction force but smaller than the separation force;
wherein the retention element is attached to the proximal section through a pair of eyes that form the inlet of the urinary catheter.

2. A telescopic device according to claim 1, wherein each of the proximal section and the distal section of the device is hollow.

3. A telescopic device according to claim 1 wherein the attachment point is located in the container.

4. A telescopic device according to claim 1 wherein the attachment point is located on the container.

5. A telescopic device according to claim 1 wherein the retention element is a string.

6. A telescopic device according to claim 5 wherein the string forms an angle of less than 45° to the direction of extension of the telescopic device.

7. A telescopic device according to claim 6 wherein the string is loose between the proximal section and the container.

8. A telescopic device according to claim 6 wherein the ends of the string are attached at the attachment point.

9. A telescopic device according to claim 1, wherein the retention element is a glue.

10. A telescopic device according to claim 1, wherein the retention element is a string attached to the proximal section by passing the string through an inlet eye of a urinary catheter.

* * * * *